United States Patent
Stebbins et al.

(10) Patent No.: US 11,364,190 B2
(45) Date of Patent: *Jun. 21, 2022

(54) ACID PERFLUORO-FREE SELF-FOAMING FACIAL CLEANSER COMPOSITION

(71) Applicant: L'OREAL, Paris (FR)

(72) Inventors: Nicholas David Stebbins, Clark, NJ (US); Susan Halpern Chirch, Basking Ridge, NJ (US); Ryuji Hara, Westfield, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/526,708

(22) Filed: Jul. 30, 2019

(65) Prior Publication Data

US 2021/0030659 A1 Feb. 4, 2021

(51) Int. Cl.
| | |
|---|---|
| *A61K 8/81* | (2006.01) |
| *A61K 8/04* | (2006.01) |
| *A61K 8/365* | (2006.01) |
| *A61K 8/44* | (2006.01) |
| *A61K 8/46* | (2006.01) |
| *A61K 8/58* | (2006.01) |
| *A61Q 19/10* | (2006.01) |

(52) U.S. Cl.
CPC ............ *A61K 8/8152* (2013.01); *A61K 8/046* (2013.01); *A61K 8/365* (2013.01); *A61K 8/442* (2013.01); *A61K 8/466* (2013.01); *A61K 8/585* (2013.01); *A61Q 19/10* (2013.01); *A61K 2800/22* (2013.01); *A61K 2800/596* (2013.01)

(58) Field of Classification Search
CPC ...... A61K 8/8152; A61K 8/046; A61K 8/365; A61K 8/442; A61K 8/466; A61K 8/585; A61K 2800/22; A61K 2800/596; A61Q 19/10
USPC .......................................................... 424/44
See application file for complete search history.

(56) References Cited

U.S. PATENT DOCUMENTS

| | | |
|---|---|---|
| 4,599,379 A | 7/1986 | Flesher et al. |
| 4,628,078 A | 12/1986 | Glover et al. |
| 4,835,206 A | 5/1989 | Farrar et al. |
| 4,849,484 A | 7/1989 | Heard |
| 5,100,660 A | 3/1992 | Hawe et al. |
| 5,741,509 A | 4/1998 | Kushner |
| 6,172,019 B1 | 1/2001 | Dehan et al. |
| 8,263,114 B2 | 9/2012 | Berlat |
| 2002/0122772 A1 | 9/2002 | Lukenbach et al. |
| 2011/0038821 A1* | 2/2011 | Ilekti ................ A61K 8/365 424/64 |
| 2016/0175209 A1* | 6/2016 | Walker ............... A61K 8/34 424/70.28 |
| 2017/0189297 A1* | 7/2017 | De Lemos ......... A61Q 19/00 |
| 2018/0280299 A1* | 10/2018 | Buge ................. A61K 8/24 |

FOREIGN PATENT DOCUMENTS

| | | |
|---|---|---|
| CA | 2011195 A1 | 8/1990 |
| EP | 228868 A2 | 7/1987 |
| JP | 2009242340 A | 10/2009 |
| WO | 01/87232 A2 | 11/2001 |
| WO | WO 200205758 A2 * | 1/2002 |

\* cited by examiner

*Primary Examiner* — Blessing M Fubara
(74) *Attorney, Agent, or Firm* — Laetitia Leproust; Robert Klemz

(57) ABSTRACT

A self-foaming cleansing composition are provided. The self-foaming composition includes a) from about 0.5% to about 10% wt. % of one or more volatile silicone oils; b) from about 0.5% to about 25% wt. % of one or more surfactants stable at low pH; c) from about at least 1.2% of one or more polymers with suspending properties; d) from about 0.5% to about 5% wt % of one or more thickeners; e) from about 0.5% to about 15% wt. % of one organic acid as cosmetic active ingredient; the self-foaming cleansing composition having a pH in between about 3.4 and 5; the self-foaming cleansing composition starting to foam immediately after application of the compositions onto the skin; wherein the foaming cleansing composition is free of perfluoro compound; and wherein the weight percentages are based on the total weight of the self-foaming cleansing composition.

12 Claims, No Drawings

ACID PERFLUORO-FREE SELF-FOAMING FACIAL CLEANSER COMPOSITION

FIELD OF THE DISCLOSURE

The present disclosure relates to acid perfluoro free self-foaming facial cleanser compositions that include a combination of volatile silicone oil, a blend of surfactants and polymers with suspending properties and one organic acid in order to obtain an acid perfluoro free self-foaming facial cleansers.

BACKGROUND

Foaming cleansing products have a cleansing action by virtue of the surfactants, which suspend the fatty residues and the pigments of, for example, make-up products. A good foaming property, rinsability, and skin-care property, for example, leaving a good feeling on the skin after rinsing off, such as skin mildness and a moisturizing sensation, are very important for cosmetic foaming cleanser products.

From the consumer's perspective, the amount of the foam directly relates to the perceived cleaning efficiency of the composition. Generally speaking, the larger the volume of foam produced and the more stable the foam, the more efficient is the perceived cleaning action of the composition. Furthermore, if other benefits can be added to the cleansers such as anti-aging, anti-wrinkle among other benefits, it is a plus for the consumers.

In view of the remarks above, there is a need to provide a self-foaming cleansing composition for cleaning the skin that foam when in contact with the skin and also bring some skin benefits at the same time, such as skin-smoothing and anti-aging benefits.

SUMMARY OF THE DISCLOSURE

The instant disclosure relates to self-foaming cleansing compositions comprising:
  a) From about 0.5% to about 10% wt. % of one or more volatile silicone oils;
  b) From about 0.5% to about 25% wt. % of one or more surfactants stable at low pH;
  c) From about at least 1.2% of one or more polymers with suspending properties;
  d) From about 0.5% to about 5% wt % of one or more thickeners;
  e) From about 0.5% to about 15% wt. % of one organic acid as cosmetic active ingredient;
  the self-foaming cleansing composition having a pH in between about 3.4 and 5;
  wherein the self-foaming cleansing composition is free of perfluoro compounds; and
  wherein the weight percentages are based on the total weight of the foaming cleansing composition.

In one or more embodiments, the foaming starts immediately after application of the composition onto the skin.

In some embodiments, the composition is a self-foaming composition.

In one or more embodiments, the self-foaming composition is self-foaming within 10 seconds after application of the cleansing composition onto the skin.

The bubbles or foam may be able to form quickly for example within less than about 10 seconds, within less than about 9 seconds, within less than about 8 seconds, within less than about 7 seconds, within less than about 6 seconds, within less than about 5 seconds, within less than about 4 seconds, within less than about 3 seconds, within less than about 2 seconds, within less than about 1 seconds after application of the cleansing composition onto the skin.

The bubbles or foam according to the instant disclosure may be long-lasting. For example, once the composition is applied to the skin and the foam is formed, the foam may remain substantially intact on the skin for a period of at least about 3 minutes, for a period of at least about 3.5 minutes, for a period of at least about 4 minutes, for a period of at least about 5 minutes, for a period of at least about 8 minutes, for a period of at least about 10 minutes.

In some embodiments, the one or more volatile silicone oils is hexamethyldisiloxane.

In some embodiments, the one or more surfactants is an amphoteric surfactant. In some embodiments, the amphoteric surfactant is a betaine-based surfactant. In some embodiments, the one or more of the surfactants are stable at low pH. In one or more embodiments, the one or more surfactants stable at low pH is an α-olefin sulfonate.

In some embodiments, the polymer with suspending properties is polyacrylate crosspolymer-6. In one or more embodiments, the polymer with suspending properties is present from about at least 1.2% wt. of the total weight of the self-foaming cleansing composition.

In some embodiments, one or more thickeners is selected from the group of xanthan gum, guar gum, biosaccharide gum, cellulose, *Sclerotium* gum, agarose, pechtin, gellan gum, ammonium polyacryloyldimethyl taurate, ammonium acryloyldimethyltaurate/VP copolymer, polyacrylamide, carbomer, and acrylates/C10-30 alkyl acrylate crosspolymer. In one or more embodiments, the thickener is ammonium polyacryloyldimethyl taurate. In some embodiments, the thickener is present from about 0.5% to about 5% wt. of the total weight of the self-foaming cleansing composition.

In some embodiments, self-foaming cleansing compositions may comprise:
  a) From about 0.8% to about 5% wt. % of hexamethyldisiloxane;
  b) From about 1% to about 20% wt. of one or more surfactants stable at low pH and selected from cocobetaine, sodium C14-16 olefin sulfonate, sultaines, betaines, alkyl polyglucosides, taurates and mixture thereof.
  c) From about at least 1.2% wt. % of one or more polymer with suspending properties is selected from polyacrylate crosspolymer-6.
  d) From about 0.5% to about 5% wt % of one or more thickeners selected from the group of xanthan gum, guar gum, biosaccharide gum, cellulose, *Sclerotium* gum, agarose, pechtin, gellan gum, ammonium polyacryloyldimethyl taurate, ammonium acryloyldimethyltaurate/VP copolymer, polyacrylamide, carbomer, and acrylates/C10-30 alkyl acrylate crosspolymer.
  e) From about 3% to about 8% wt. % of glycolic acid;
  the self-foaming cleansing composition starting to foam immediately after application of the compositions onto the skin;
  wherein the foaming cleansing composition is free of perfluoro compound;
  wherein pH is in between about 3.4 and 5;
  wherein the weight percentages are based on the total weight of the self-foaming cleansing composition.

The self-foaming cleansing compositions are useful for treating the skin, in particular the skin of the face. The compositions can be used as a facial wash, and/or makeup remover, as the products are particularly effective at cleansing and exfoliating the skin, as well as improving photo damaged skin, hyperpigmentation, acne vulgaris, rosacea, wrinkles, fine lines or superficial scars.

Some aspects of the instant disclosure can include a method for cleansing the skin comprising applying the composition to the skin and removing at least a portion of the composition from the skin.

The methods generally include applying the self-foaming cleansing compositions to the skin, cleansing the face and improving photo damaged skin, hyperpigmentation, acne vulgaris, rosacea, wrinkles, fine lines or superficial scars.

The self-foaming cleansing compositions of the instant disclosure provide unexpected level of foaming as well as an unexpected lastingness once in contact with the skin. The compositions also provide some benefits of anti-aging benefits, such as photo damaged skin, hyperpigmentation, acne vulgaris, rosacea, wrinkles, fine lines or superficial scars.

It is to be understood that both the foregoing general description and the following detailed description are exemplary and explanatory only, and are not restrictive of the invention.

DETAILED DESCRIPTION OF THE DISCLOSURE

The self-foaming cleansing compositions of the instant disclosure, in their broadest sense, typically include the following:
  a) From about 0.5% to about 10% wt. % of one or more volatile silicone oils;
  b) From about 0.5% to about 25% wt. % of one or more surfactants stable at low pH;
  c) From about at least 1.2% of one or more polymers with suspending properties;
  d) From about 0.5% to about 5% wt. % of one or more thickeners;
  e) From about 0.5% to about 15% wt. % of one organic acid as cosmetic active ingredient;
  the self-foaming cleansing composition having a pH in between about 3.4 and 5;
  the self-foaming cleansing composition starting to foam immediately after application of the compositions onto the skin;
  wherein the self-foaming cleansing composition is free of perfluoro compound; and
  wherein the weight percentages are based on the total weight of the foaming cleansing composition.

As used herein, the term "suspending properties" means that it imparts a particular yield value that is sufficient to overcome the effect of gravity or buoyancy of particles or water-insoluble droplets, and is thus able to effectively suspend those particles or droplets.

The self-cleansing compositions described herein may be free or essentially free of perfluoro compounds.

As used herein, the term "free of perfluoro compound" means that, while it is preferable that no perfluoro is present in the composition of the invention, it is possible to have very small amounts of perfluoro in the compositions, provided that these amounts do not materially affect the advantageous properties of the composition. Most preferably, the compositions contain no perfluoro. To the extent any perfluoro is present in the compositions, it is present at an amount of less than about 2.0% by weight, typically less than about 1.5% by weight, typically less than about 1.0% by weight, typically less than about 0.5% by weight, more typically less than about 0.1% by weight, based on the total weight of the composition. To the extent present, the perfluoro in such compositions are typically contributed by components other than the perfluoro compound.

The self-foaming cleansing compositions disclosed herein foam immediately after application of the composition onto the skin. In some embodiments, the foaming composition is self-foaming within 10 seconds after application of the cleansing composition onto the skin. The foaming, then, last at least about 3 minutes, at least about 3.5 minutes or more.

As used herein, the term "self-bubbling" or "self-foaming" means that it is a composition that exhibits bubbles and/or foam only when applied in a thin layer to the skin without the additional of any other exterior stimuli.

As used herein, the term "foam" means the ability of a composition to produce foam.

As used herein, the term "foam" and "bubble" are used interchangeably throughout the instant disclosure.

The bubbles or foam may be able to form quickly for example within less than about 10 seconds, within less than about 9 seconds, within less than about 8 seconds, within less than about 7 seconds, within less than about 6 seconds, within less than about 5 seconds, within less than about 4 seconds, within less than about 3 seconds, within less than about 2 seconds, within less than about 1 seconds after application of the cleansing composition onto the skin.

The bubbles or foam according to the instant disclosure may be long-lasting. For example, once the composition is applied to the skin and the foam is formed, the foam may remain substantially intact on the skin for a period of at least about 3 minutes, for a period of at least about 3.5 minutes, for a period of at least about 4 minutes, for a period of at least about 5 minutes, for a period of at least about 8 minutes, for a period of at least about 10 minutes.

Volatile Silicone Oil

The self-foaming cleansing compositions described herein may contain one or more volatile silicone oils. In some embodiments, the one or more volatile silicone oils, may be, for example an hexamethyldisiloxane.

Examples of volatile silicones, may be, for instance volatile linear or cyclic silicone oils, especially those with a viscosity of less than or equal to 8 centistokes (cSt) (8×10−6 m2/s), at 25° C. and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethyl-cyclo-penta-siloxane, cyclohexasiloxane, dodecamethylcyclohexasiloxane, heptamethylhexyltrisiloxane, hepta-methyl-octyl-trisiloxane, hexamethyldisiloxane, octamethyltrisiloxane, decamethyl-tetrasiloxane and dodecamethylpentasiloxane, and mixtures thereof.

The total amount of volatile silicone oils may be present in an amount from about 0.5%, 0.6%, 0.7%, 0.8%, 0.95,1%, 1.1%, 1.2%, 1.4%, 1.5%, 1.6%, 1.8%, 2%, 2.4%, 2.6%, 2.8%, 3%, 3.2%, 3.4%, 3.6%, 3.8% to about 3.8%, 4%, 4.1%, 4.2%, 4.3%, 4.4%, 4.5%, 4.6%, 4.7%, 4.8%, 4.9%, 5%, 5.2%, 5.4%, 5.6%, 5.8%, 6%, 6.2%, 6.4%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8% or 10% wt. of the total weight of the self-foaming cleansing composition.

Surfactants Stable at Low pH

Surfactants in the composition include a single surfactant or a mixture of surfactants (often surfactant powders or in other easily used forms (liquid)). The compositions can have an acidic pH. For example, in some cases, the pH may be in the range of 2 to 5, 3 to 4.5, or 3.5 to 4. Consequently, the surfactants need to be stable at low pH. In one embodiment, the composition includes one or more ionic surfactants that includes anionic or amphoteric surfactants.

In some embodiments, the one or more surfactants stable at low pH may be selected from coco-betaine, sodium C14-16 olefin sulfonate, sultaines, betaines, alkyl polyglucosides, taurates and mixture thereof.

Amphotheric Surfactant

Examples of amphoteric surfactants include surfactants selected from these classes of surfactants: amphocarboxylates, alkyl betaines, amidoalkyl betaines, amphophosphates, phosphobetaines, pyrophosphobetaines, carboxyalkyl polyamines, and amidoalkyl sultaines. In selected embodiments, the preferred surfactants are those having C10 to C16 in their fatty acyl part.

In alternative embodiments, the surfactant may include suitable nonionic surfactants including alkyl polyglucoside having alkyl groups from C10 to C16, and optionally cocoamidopropyl amine oxide.

Anionic Surfactants

Examples of anionic surfactants include surfactants selected from these classes of surfactants: alkyl sulfates, alkyl ether sulfates, alkyl monoglyceride sulfates, alkyl monoglyceride sulfonates, alkylaryl sulfates, alkyl sulfosuccinamates, alkyl ether carboxylates, alkyla idoether carboxylates, fatty acyl sarcosinates, fatty acyl glutamates, and alkyl phosphates.

In some embodiments, one surfactant can be, for example, a compound selected from the group consisting of sodium lauroyl glutamate and sodium lauryl sulfate, Examples of anionic surfactants include surfactants selected from these classes of surfactants: alkyl sulfates, alkyl ether sulfates, alkyl monoglyceride sulfates, alkyl monoglyceride sulfonates, alkylaryl sulfates, alkyl sulfosuccinamates, alkyl ether carboxylates, alkyla idoether carboxylates, fatty acyl taurates, fatty acyl sarcosinates, fatty acyl glutamates, and alkyl phosphates. Alternative surfactants may include or be combined with foaming surfactants or foaming agents suitable for use in foaming skin cleansers or on skin cleaning fibrous pads when mixed with water. The foaming action provided surfactant use aids in exfoliation of skin cells and additional cleaning benefits allowing a crisp clean feel following wash-off by a user.

In alternative embodiments, the surfactant may include suitable nonionic surfactants including alkyl polyglucoside having alkyl groups from C10 to C16.

Other Surfactants

According to the instant disclosure, these surfactants can be chosen from salts, for example, alkali metal salts such as sodium salts, ammonium salts, amine salts, amino alcohol salts and alkaline-earth metal salts.

Examples of alkaline-earth metal salts include magnesium salts of the following types of compounds: acyl taurates, acyl amino acids, acyl sarcosinates, sulfonates, and sulfoacetates, the alkyl and acyl groups of all these compounds comprising from 6 to 24 carbon atoms (saturated or unsaturated, linear or branched).

Non-limiting examples of acyl amino acids useful in the compositions of the invention include those having the following formula (I):

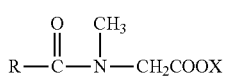

(I)

in which

R is a linear or branched, saturated or unsaturated $C_8$-$C_{16}$ and more preferentially $C_{12}$-$C_{18}$ alkyl chain;

X is an organic cation, for instance an alkanolamine such as triethanolamine, or a mineral cation, for instance an alkali metal such as sodium or potassium, or alternatively ammonia.

Among the preferred radicals R, mention may be made of stearyl, myristyl, oleyl, lauryl and cocoyl.

Among the N-acyl sarcosinates that may be used according to the invention, mention may be made of sodium lauroyl sarcosinate (INCI name: Sodium lauroyl sarcosinate) sold under the name Sarkosyl NL 97® by the company Ciba or sold under the name Oramix L 30® by the company SEPPIC, or sold under the name Amin LS30 L by the company Guangzhou Tinci Materials; sodium myristoyl sarcosinate (INCI name: Sodium myristoyl sarcosinate) sold under the name Nikkol Sarcosinate MN® by the company Nikkol, sodium palmitoyl sarcosinate (INCI name: Sodium palmitoyl sarcosinate) sold under the name Nikkol Sarcosinate PN® by the company Nikkol.

Use will be made more particularly of sodium N-lauroyl sarcosinate (INCI name: Sodium lauroyl sarcosinate).

Non-limiting examples of taurates useful in the compositions of the invention include those having the following formula (II):

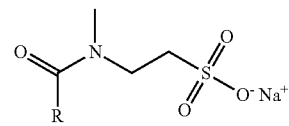

(II)

wherein R is selected from H or an alkyl chain that has 1-24 carbon atoms, said chain being saturated or unsaturated, linear or branched.

A particular taurate that can be used in the current compositions is sodium methyl cocoyl taurate.

Non-limiting examples of sulfonates useful in the compositions of the invention include those having the following formula (VI):

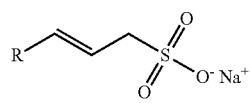

(VI)

wherein R is selected from H or an alkyl chain that has 1-24 carbon atoms, said chain being saturated or unsaturated, linear or branched.

A particular sulfonate that can be used in the current compositions is sodium $C_{14-16}$ olefin sulfonate.

Non-limiting examples of sulfoacetates useful in the compositions of the invention include those having the following formula (VII):

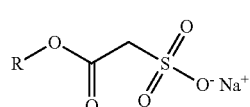

(VII)

wherein R is as defined above for the sulfonates.

A particular sulfoacetate that can be used in the current compositions is sodium lauryl sulfoacetate.

According to one embodiment, the anionic surfactant that is most preferred in the instant disclosure is acyl amino acids useful in the compositions of the invention include those having the following formula (I) as described above, more preferably N-acyl sarcosinates, even more preferably sodium lauroyl sarcosinate (INCI name: Sodium lauroyl sarcosinate).

Non-Sulfate Anionic Surfactants

Useful non-sulfate anionic surfactants include, but are not limited to acyl amino acids (such as acyl taurates, acyl glutamates, and acyl sarcosinates), alkyl sulfonates, alkyl sulfoacetates, alkoxylated monoacids, salts thereof, and a mixture thereof.

Linear α-Olefin Sulfonates

In some cases, the surfactant may include one linear α-olefin sulfonate and may be, for example, selected from those of formula (VIII):

R—CH2—CH=CH—(CH2)$_n$—SO3M    (VIII)

in which:

R is a saturated linear alkyl radical comprising from 4 to 30 carbon atoms, especially from 6 to 20 carbon atoms, or even from 8 to 18 carbon atoms and better still from 10 to 14 carbon atoms;

n is an integer between 0 and 10, preferably between 1 and 4 and better still n=1;

M is a cosmetically acceptable cation, chosen especially from the ammonium cation, cations derived from alkali metals or alkaline-earth metals, cations derived from organic amines such as alkanolamines; preferably those derived from alkali metals; and especially Na+ or K+.

Preferably, R represents a linear alkyl radical comprising from 8 to 14 carbon atoms, especially from 10 to 12 carbon atoms.

Preferably, M is derived from an alkali metal, especially Na+ or K+.

Preferably, the linear alkene sulfonate according to the present invention has the structure of formula (iX):

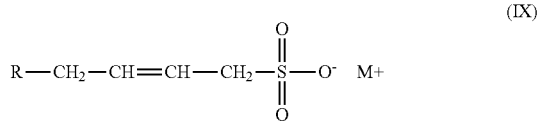

in which:

R is a saturated linear alkyl radical comprising from 4 to 20 carbon atoms, especially from 6 to 18 carbon atoms, or even from 8 to 14 carbon atoms and better still from 10 to 12 carbon atoms;

M is a cosmetically acceptable cation, chosen especially from the ammonium cation, cations derived from alkali metals or alkaline-earth metals, cations derived from organic amines such as alkanolamines; preferably those derived from alkali metals or alkali metals; and especially Na+ or K+.

Preferably, the linear α-olefin sulfonates according to the instant disclosure are chosen from linear α-olefin sulfonates comprising 8 to 28 carbon atoms, especially from 10 to 24 carbon atoms, better still from 12 to 20 carbon atoms, in particular from 14 to 18 carbon atoms; in particular, of alkali metals, especially of sodium, for example sodium C14-C16 olefin sulfonate.

Said α-olefin sulfonates are known compounds and are described especially in Ullmann's Encyclopedia of Industrial Chemistry or in U.S. Pat. No. 8,211,850. These compounds are generally obtained by sulfonation of long-chain α-olefins.

The total amount of one or more surfactants may be present from about 0.5%, 0.6%, 0.7%, 0.8%, 0.9%, 1%, 1.1%, 1.2%, 1.3%, 1.4%, 1.5%, 1.6%, 1.7%, 1.8%, 1.9% 2%, 2.1%, 2.2%, 2.5%, 3%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8%, 10% to about 10%, 10.2%, 10.4%, 10.6%, 10.8%, 11%, 11.2%, 11.4%, 11.6%, 11.8%, 12%, 12.2%, 12.4%, 12.6%, 12.8%, 13%, 13.2%, 13.4%, 13.6%, 13.8%, 14%, 14.2%, 14.4%, 14.6%, 14.8%, 15%, 15.2%, 15.4%, 15.6%, 15.8%, 16%, 16.2%, 16.4%, 16.6%, 16.8%, 17%, 17.2%, 17.4%, 17.6%, 17.8%, 18%, 18.2%, 18.4%, 18.6%, 18.8%, 19%, 19.2%, 19.4%, 19.6%, 19.8%, 20%, 20.2%, 20.4%, 20.6%, 20.8%, 21%, 21.2%, 21.4%, 21.6%, 21.8%, 22%, 22.2%, 22.4%, 22.6%, 22.8%, 23%, 23.2%, 23.4%, 23.6%, 23.8%, 24%, 24.2%, 24.4%, 24.6%, 24.8%, or 25% wt. of the total weight of the self-foaming cleansing.

Rheology Modifiers

Polymer with Suspending Properties

As mentioned above, the cleansing compositions typically include a polymer with suspending properties selected from the group consisting of polyacrylate crosspolymer-1, polyacrylate crosspolymer-6, polyacrylate crosspolymer-9, polyacrylate crosspolymer-11, and the mixtures thereof.

The crosslinked polyacrylate polymers may be present in an amount from about 1.2% to about 7% by weight based on the total weight of the composition.

Non-limiting examples of various types of rheology modifiers include crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379 and EP 228,868, which are all incorporated herein by reference in their entirety.

More particularly, the polymer can be used in the instant disclosure is 2-methyl-2-[(1-oxo-2-propenyl]amino]-1-propanesulfonic acid, partially or totally salified in the form of ammonium salt, of N, N-dimethylacrylamide and lauryl acrylate and crosslinked with trimethylol tetraethoxylated propanetriacrylate under the INCI name: Polyacrylate Crosspolymer-6, such as the product sold under the trade name SEPIMAX ZEN® by Seppic.

The total amount of one or more polymers with suspending properties of the instant disclosure may be employed in an amount from about 1.2%, 1.3%, 1.4%, 1.5%, 1.6%, 1.7% 1.8%, 1.9% 2%, 2.1%, 2.2%, 2.5%, to about 3%, 3.4%, 3.6%, 3.8%, 4%, 4.2%, 4.4%, 4.6%, 4.8%, 5%, 5.2%, 5.4%, 5.6%, 5.8%, 6%, 6.2%, 6.5%, or 7% wt. of the total weight of the self-foaming cleansing composition.

Thickeners

The self-foaming cleansing compositions described herein may include one or more thickeners. The thickeners may be in an amount from about 0.5%, 0.6%, 0.7%, 0.8%, 0.9%, 1.0%, 1.5% to about 1.5%, 2%, 2.5%, 3%, 3.5%, 4%, 4.5%, or 5 wt. % of the total weight of the self-foaming cleansing composition.

The one or more thickeners may be polymeric thickeners selected from the group consisting of ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some cases, the composition includes ammonium polyacryloyldimethyl taurate and/or sodium polyacrylate. Additionally, the one or more thickeners may include xanthan gum, guar gum, biosaccharide gum, cellulose, acacia Seneca gum, *Sclerotium* gum, agarose, pechtin, gellan gum, hyaluronic acid.

Many thickeners are water-soluble, and increase the viscosity of water or form an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol®. 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of useful crosslinked nonionic polyacrylate polymers and crosslinked cationic polyacrylate polymers are those described in U.S. Pat. Nos. 5,100,660, 4,849,484, 4,835,206, 4,628,078, 4,599,379 and EP 228,868, which are all incorporated herein by reference in their entirety.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

The compositions may also contain thickening and texturising gels of the type as exemplified by the product range called Lubrajel® from United Guardian. These gels have moisturizing, viscosifying, stabilizing properties.

d. Polysaccharides

A wide variety of polysaccharides can be useful herein. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation.

Other useful polysaccharides include scleroglucans comprising a linear chain of (1-3) linked glucose units with a (1-6) linked glucose every three units, a commercially available example of which is Clearogel™. CS11 from Michel Mercier Products Inc.

e. Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, *Sclerotium* gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Cosmetic Active Ingredients
Organic Acid

The composition according to the instant disclosure comprises at least one organic acid as cosmetic active ingredient.

Many organic acids can be used as cosmetic active ingredient to bring specific efficacy for example anti-Acne effect and/or peeling effect.

Peeling is well-known approach to improve the appearance and/or the texture of the skin and/or of the scalp, in particular improving the radiance and the homogeneity of the complexion and/or reducing the visible and/or tactile irregularities of the skin, and in particular for improving the surface appearance of the skin, for reducing actinic lentigo, acne marks and chickenpox marks, and also for preventing, reducing or combating the signs of skin aging, and in particular for smoothing out the irregularities of the skin's texture, such as wrinkles and fine lines.

Peeling has the effect of removing a superficial part of the skin (epidermis and possibly superficial layer of the dermis).

Organic acid can be used as anti-acne and/or peeling agent is preferably selected from saturated and unsaturated monocarboxylic acids, saturated and unsaturated dicarboxylic acids, saturated and unsaturated tricarboxylic acids; α-hydroxy acids and β-hydroxy acids of monocarboxylic acids; α-hydroxy acids and β-hydroxy acids of dicarboxylic acids; α-hydroxy acids and β-hydroxy acids of tricarboxylic acids; keto acids, α-keto acids, β-keto acids of polycarboxylic acids, of polyhydroxymonocarboxylic acids, of polyhydroxydicarboxylic acids or of polyhydroxytricarboxylic acids; and (3-hydroxy-2-pentylcyclopentyl)acetic acid.

Preferred α-hydroxy acids that are exemplary include: glycolic acid, citric acid, lactic acid, tartaric acid, malic acid or mandelic acid.

Preferred β-hydroxy acids are selected from: salicyclic acid and derivatives thereof, in particular 5-n-octanoylsalicylic acid.

Those skilled in the art will be able to define the required amount of organic acid present in the composition according to the invention in order to obtain the desired effect on the skin.

The organic acid may be in an amount from about 0.5%, 1.0%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7% to about 7%, 7.2%, 7.4%, 7.6%, 7.8%, 8%, 8.2%, 8.4%, 8.6%, 8.8%, 9%, 9.2%, 9.4%, 9.6%, 9.8%, 10%, 10.2%, 10.4%, 10.6%, 10.8%, 11%, 11.2%, 11.6%, 11.8%, 12%, 12.2%, 12.6%, 12.8%, 13%, 13.2%, 13.4%, 13.6%, 13.8%, 14%, 14.2%, 14.4%, 14.6%, 14.8%, 15% wt. of the total weight of the self-foaming cleansing.

Optional Components

In one embodiment, the composition may include optional components selected from the group consisting of actives, fragrance, preservatives, and combinations thereof. The actives are selected from the group consisting of butylated hydroxytoluene, tocopherol, tocopheropl derivatives, tocotrienol, tocotrienol derivatives, ascorbic acid, ascorbic acid derivatives, ascorbyl palmitate, vitamin E, vitamin C, and combinations thereof.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

EXAMPLE 1

Acid Perfluoro Free Self-Foaming Cleansing Compositions

The following Examples are provided for illustrative purposes only, and are not intended to be limiting.

TABLE 1

| | | Inventive Examples | | | |
|---|---|---|---|---|---|
| Claim Component | Cosmetic type | INCI US | Inv. Ex. 1 | Inv. Ex. 2 | Inv. Ex. 3 |
| a | SILICON | DISILOXANE | 2 | 2 | 2 |
| b | SURFACTANT | COCO-BETAINE | 3.6 | 4.8 | 4.8 |
| | SURFACTANT | SODIUM C14-16 OLEFIN SULFONATE | 4 | 5.6 | 5.6 |
| c | POLYMER | POLYACRYLATE CROSSPOLYMER-6 | 1.5 | 1.8 | 1.8 |
| | THICKENER | AMMONIUM POLYACRYLOYLDIMETHYL TAURATE | 2.5 | 1.8 | 1.2 |
| | ACTIVE | GLYCOLIC ACID (AHA) | 3.5 | 6 | 6 |
| | Preservatives, pH adjusters, solvents | | 0.5-5 | 0.5-5 | 0.5-5 |
| | SOLVENT | GLYCERIN | 5 | 6 | 6 |
| | SOLVENT | WATER | Q.S | Q.S. | Q.S. |

In making the formulations in the above table, the following procedure was used.

Generally, the polymer(s) were added to water until well-dispersed, then remaining solvents were mixed with the preservatives until they were dissolved. The active was then added and the pH was adjusted to the proper value. Surfactant(s) were then added and batch was stirred until uniform. Finally, the silicone component was added while simultaneously mixing and homogenizing the batch to properly disperse the silicones. Once homogenous and well-dispersed, the batch was complete.

EXAMPLE 2

Evaluation of the Polymers

Experiments incorporating different types of Acrylates were conducted to observe their different behaviors depending on the pH of the formula described in the instant disclosure. The Results are presented in Table 2 below.

TABLE 2

| | Evaluation of Polymers at different pH | | | |
|---|---|---|---|---|
| Formula Iteration | Polymer used for suspension | AHA Amount | pH of formula | Result |
| 1 | Acrylates Copolymer | 0% | 6.2 | Stable formula |
| 2 | Acrylates Copolymer | 1.0% | 4.2 | Unstable formula; too thin and poor suspension |

TABLE 2-continued

Evaluation of Polymers at different pH

| Formula Iteration | Polymer used for suspension | AHA Amount | pH of formula | Result |
|---|---|---|---|---|
| 3 | Acrylates Copolymer | 3.5% | 3.6 | Unstable formula; too thin and poor suspension |
| 4 | Polyacrylates Crosspolymer-6 | 3.50% | 3.6 | Stable formula |
| 5 | Polyacrylates Crosspolymer-6 | 8.0% | 3.6 | Stable formula |

Data showed that the acrylate copolymer used in a non-acidic formula is insufficient to make a stable and effective formula. In the cases above, it was shown that the acrylate copolymer was not suitable to use in the instant disclosure. Thus, a different, specific type of polymer is required.

Evaluation of the Combination of Polymers

Experiments incorporating different types of polymers and combinations of polymers were conducted to observe their different behaviors and to show the importance of determining the best combinations of the polymers with suspending and thickening properties in order to achieve the unexpected self-foaming results as well as a stable composition when there is presence of an acid skin active such AHA as described in the instant disclosure.

Results are reported in Table 3 below.

TABLE 3

Inventive and Comparative Examples

| Examples | Polymer 1 | Polymer 2 | AHA Amount | pH | Result |
|---|---|---|---|---|---|
| Inv. Ex 1 | Polyacrylates Cross polymer-6 | AMPS ®* | 3.5% | 3.6 | Stable formula |
| Inv. Ex. 2 | Polyacrylates Cross polymer-6 | AMPS ®* | 6.0% | 3.6 | Stable formula |
| Comp. Ex. 1 | Acrylates Copolymer | Acrylates/Beheneth-25 Methacrylate Copolymer | 3.5% | 3.6 | Unstable formula; too thin and poor suspension |
| Comp. Ex. 2 | Acrylates Copolymer | None | 1.0% | 3.6 | Unstable formula; too thin and poor suspension |
| Comp. Ex. 3 | Acrylates Copolymer | None | 3.5% | 3.6 | Unstable formula; too thin and poor suspension |
| Comp. Ex. 4 | Sodium Acryloyldimethyltaurate/VP Crosspolymer | PEG-120 Methyl Glucose Dioleate | 3.5% | 3.6 | Unstable formula, separates |
| Comp. Ex.5 | Polyacrylates Cross polymer-6 | None | 3.5% | 3.6 | Formula too thin, poor suspension over time |
| Comp. Ex. 6 | AMPS ®* | None | 3.5% | 3.6 | Unstable formula, poor suspension |
| Comp. Ex. 7 | Acrylates/Beheneth-25 Methacrylate Copolymer | AMPS ®* | 3.5% | 3.6 | Unstable Formula |
| Comp. Ex. 8 | Carbomer | PEG-120 Methyl Glucose Dioleate | 3.5% | 3.6 | Unstable Formula, poor suspension |

*= AMPS ® = Ammonium Polyacryloydimethyl Taurate

Results Analysis

In order to evaluate the combinations of polymers with suspending properties that would work in an acidic environment several polymer combinations have been tested and are presented in Table 3 above.

According to Table 3, Inventive Examples 1 and 2 which included the combination of polyacrylate crosspolymer-6 with suspending properties and AMPS® with thickening properties, and contained AHA components at different concentration exhibited good stability while maintaining the self-foaming property at a pH of 3.6.

On the other hand, Comparative Example 1 which included the combination of acrylate copolymer and Acrylates/Beheneth-25 Methacrylate Copolymer with suspending and thickening properties, and contained the AHA component, at a pH of 3.6 showed an unstable formula, too thin and with poor suspension. Comparative Example 2 which included only the acrylate copolymer with suspending properties with 1% of AHA component, but still at a pH of 3.6 showed an unstable formula, too thin and with poor suspension. Comparative Example 3 which included only the acrylate copolymer with suspending properties with 3% of AHA component, at a pH of 3.6 showed an unstable formula, too thin and with poor suspension. Comparative Example 4 which included Sodium Acryloyldimethyltaurate/VP Crosspolymer and PEG-120 Methyl Glucose Dioleate with suspending properties with 3% of AHA component, at a pH of 3.6 showed an unstable formula and separate. Comparative Example 5 which included only Polyacrylates Crosspolymer-6 with suspending properties showed a formula too thin as well as a poor suspension over time. A similar conclusion was observed with Comparative Example 6, which includes only AMPS® with thickening properties. The Comparative Example 7 which includes Acrylates/Beheneth-25 Methacrylate Copolymer with suspending and AMPS with thickening properties showed an unstable formula. The Comparative Example 8 whicincluded Carbomer and PEG-120 Methyl Glucose Dioleate h with suspending properties showed an unstable formula and a poor suspension.

Due to the low pH, but also due to the presence electrolytes, and surfactants, most polymers systems did not work to thicken and suspend the volatile silicone oil present in the formula. The results above confirm this statement and allowed to determine the best combination of polymers that would work in the acidic environment of the formula.

The results above demonstrated the need of the combination of two polymers, one with suspending properties and one with thickening properties. It was shown that it was necessary to have both polymers present. Indeed, the use of only one, like in Comp. Ex. 5 and Comp. Ex. 6 demonstrated unstable formula. The combination of the two polymers demonstrated a surprising stable formula at an acidic pH.

EXAMPLE 3 pH Study

A study of the pH was performed. The results showed that if the pH is above 5, the composition is stable and foaming. However, the AHA component would be mostly in salt forma rather than acid form, and efficacy would be very low for the AHA. The compositions need to have an acidic pH due to the presence of the acidic skin care active. For example, in some cases, the pH may be in the range of 2 to 5, 3 to 4.5, or 3.5 to 4.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A self-foaming cleansing composition comprising:
   a) From about 0.5% to about 10% wt. % of one or more volatile silicone oils;
   b) From about 0.5% to about 25% wt. % of one or more surfactants stable at low pH;
   c) From about at least 1.2% of one or more polymers with suspending properties is selected from the group consisting of polyacrylate crosspolymer-1, polyacrylate crosspolymer-6, polyacrylate crosspolymer-9, polyacrylate crosspolymer-11, and the mixtures thereof;
   d) From about 0.5% to about 3.8% wt. % of one or more thickeners;
   e) From about 3% to about 15% wt. % of one organic acid as cosmetic active ingredient;
   the self-foaming cleansing composition having a pH in between about 3.4 and 5;
   the self-foaming cleansing composition starting to foam immediately after application of the compositions onto the skin;
   wherein the self-foaming cleansing composition is free of perfluoro compound; and
   wherein the weight percentages are based on the total weight of the foaming cleansing composition.

2. The self-foaming cleansing composition of claim 1, wherein the one or more volatile silicone oils is hexamethyldisiloxane.

3. The self-foaming cleansing composition of claim 1, wherein the one or more surfactants is an amphoteric surfactant.

4. The self-foaming cleansing composition of claim 3, wherein the amphoteric surfactant is a betaine-based surfactant.

5. The self-foaming cleansing composition of claim 1, wherein one or more of the surfactants are stable at low pH.

6. The self-foaming cleansing composition of claim 5, wherein the one or more surfactants stable at low pH is an α-olefin sulfonate.

7. The self-foaming cleansing composition of claim 1, wherein the polymer with suspending properties is polyacrylate crosspolymer-6.

8. The self-foaming cleansing composition of claim 1, wherein the polymer with suspending properties is present from about at least 1.2% wt. of the total weight of the self-foaming cleansing composition.

9. The self-foaming cleansing composition of claim 1, wherein the thickener is ammonium polyacryloyldimethyl taurate.

10. A method for cleansing skin comprising applying the composition of claim 1 to the skin and removing at least a portion of the composition from the skin.

11. A method for cleansing face comprising applying the cleansing composition of claim 1 to the face to cleanse the face and to improve photo damaged skin, hyperpigmentation, acne vulgaris, rosacea, wrinkles, fine lines or superficial scars.

12. A self-foaming cleansing composition comprising:
   a) From about 0.8% to about 5% wt. % of hexamethyldisiloxane;
   b) From about 1% to about 20% wt. of one or more surfactants stable at low pH and selected from cocobetaine, sodium C14-16 olefin sulfonate, sultaines, betaines, alkyl polyglucosides, taurates and mixture thereof,
   c) From about at least 1.2% wt. % of one or more polymer with suspending properties is selected from polyacrylate crosspolymer-6;
   d) From about 0.5% to about 3.8% wt % of one or more thickeners is selected from the group of xanthan gum, guar gum, biosaccharide gum, cellulose, *Sclerotium* gum, agarose, pechtin, gellan gum, ammonium polyacryloyldimethyl taurate, ammonium acryloyldimethyltaurate/VP copolymer, polyacrylamide, carbomer, and acrylates/C10-30 alkyl acrylate crosspolymer,
   e) From about 3% to about 8% wt. % of glycolic acid;
   the self-foaming cleansing composition starting to foam immediately after application of the compositions onto the skin;
   wherein the foaming cleansing composition is free of perfluoro compound;
   wherein pH is in between about 3.4 and 5;
   wherein the weight percentages are based on the total weight of the self-foaming cleansing composition.

* * * * *